(12) United States Patent
Matsuzaki

(10) Patent No.: US 8,765,756 B2
(45) Date of Patent: Jul. 1, 2014

(54) PLANT DISEASE CONTROLLING COMPOSITION AND USE THEREOF

(75) Inventor: Yuichi Matsuzaki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/816,067

(22) PCT Filed: Aug. 9, 2011

(86) PCT No.: PCT/JP2011/068200
§ 371 (c)(1),
(2), (4) Date: Feb. 8, 2013

(87) PCT Pub. No.: WO2012/020778
PCT Pub. Date: Feb. 16, 2012

(65) Prior Publication Data
US 2013/0131067 A1 May 23, 2013

(30) Foreign Application Priority Data

Aug. 10, 2010 (JP) .................. 2010-179304

(51) Int. Cl.
*A01N 43/58* (2006.01)
*A01N 43/56* (2006.01)
(52) U.S. Cl.
USPC ........................................................ 514/247
(58) Field of Classification Search
None
See application file for complete search history.

(56) References Cited

U.S. PATENT DOCUMENTS

| 4,742,074 A | | 5/1988 | Nishida et al. | |
| 5,093,347 A | * | 3/1992 | Graneto et al. | 514/406 |
| 2008/0194566 A1 | | 8/2008 | Morishita et al. | |
| 2008/0275050 A1 | | 11/2008 | Morishita et al. | |
| 2009/0281337 A1 | | 11/2009 | Morishita et al. | |
| 2010/0144674 A1 | | 6/2010 | Trah et al. | |

FOREIGN PATENT DOCUMENTS

| CA | 1262735 A1 | | 11/1989 | | |
| CN | 101262764 A | | 9/2008 | | |
| CN | 101535275 A | | 9/2009 | | |
| EP | 0199822 A1 | | 11/1986 | | |
| EP | 1775290 A1 | * | 4/2007 | ........... | C07D 237/08 |
| EP | 2011396 A1 | * | 1/2009 | ............. | A01N 43/58 |
| EP | 1767529 B1 | | 5/2009 | | |
| JP | 61-106559 A | | 5/1986 | | |
| JP | 61-280480 A | | 12/1986 | | |
| JP | 62-010066 A | | 1/1987 | | |
| JP | 62-096472 A | | 5/1987 | | |
| JP | 2006-022084 A | | 1/2006 | | |
| JP | 2006-045192 A | | 2/2006 | | |
| KR | 10-1992-0003893 B1 | | 5/1992 | | |
| WO | 8602641 A1 | | 5/1986 | | |
| WO | 9212970 A1 | | 8/1992 | | |
| WO | WO 9212970 A1 | * | 8/1992 | ........... | C07D 231/14 |
| WO | 2005121104 A1 | | 12/2005 | | |
| WO | 2006001175 A1 | | 1/2006 | | |

OTHER PUBLICATIONS

Int'l Preliminary Report on Patentability issued Mar. 21, 2013 in Int'l Application No. PCT/JP2011/068200.
Int'l Search Report issued Nov. 8, 2011 in Int'l Application No. PCT/JP2011/068200.
Office Action issued Feb. 26, 2014 in CN Application No. 201180038654.8.

\* cited by examiner

*Primary Examiner* — Dennis Heyer
*Assistant Examiner* — Daniel M Podgorski
(74) *Attorney, Agent, or Firm* — Panitch Schwarze Belisario & Nadel LLP

(57) ABSTRACT

A plant disease controlling composition, containing a carboxamide compound represented by formula (I):

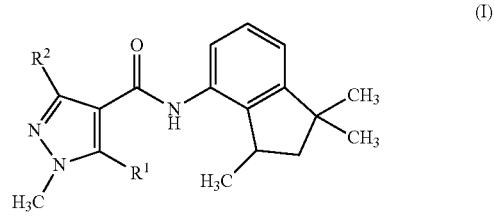

wherein $R^1$ represents a hydrogen atom or a methyl group and $R^2$ represents a methyl group, a difluoromethyl group or a trifluoromethyl group; and
a pyridazine compound represented by formula (II)

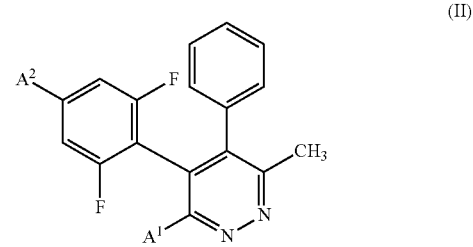

wherein $A^1$ represents a chlorine atom, a bromine atom, a cyano group or a methyl group, and $A^2$ represents a hydrogen atom or a fluorine atom.

6 Claims, No Drawings

PLANT DISEASE CONTROLLING COMPOSITION AND USE THEREOF

CROSS-REFERENCE TO RELATED APPLICATION

This application is a Section 371 of International Application No. PCT/JP2011/068200, filed Aug. 9, 2011, which was published in the Japanese language on Feb. 16, 2012, under International Publication No. WO 2012/020778 A1, and the disclosure of which is incorporated herein by reference.

TECHNICAL FIELD

The present invention relates to a plant disease controlling composition and use thereof.

BACKGROUND ART

Conventionally, many compounds for controlling plant diseases have been developed and put into practical use (see, for example, Patent Literatures 1, 2, 3 and 4).

CITATION LIST

Patent Literature

Patent Literature 1: International Publication No. WO86/02641
Patent Literature 2: International Publication No. WO92/12970
Patent Literature 3: International Publication No. WO2005/121104
Patent Literature 4: International Publication No. WO2006/001175

SUMMARY OF INVENTION

Technical Problem

An object of the present invention is to provide a composition having an excellent efficacy in controlling plant diseases.

Solution to Problem

The present invention primarily provides a plant disease controlling composition containing a carboxamide compound represented by the following formula (I) and a pyridazine compound represented the following formula (II). The composition has an excellent efficacy in controlling plant diseases.

More specifically, the present invention is as follows.
[1] A plant disease controlling composition, containing a carboxamide compound represented by formula (I):

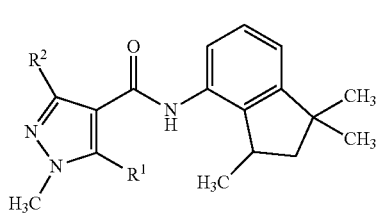

(I)

wherein $R^1$ represents a hydrogen atom or a methyl group and $R^2$ represents a methyl group, a difluoromethyl group or a trifluoromethyl group, and
a pyridazine compound represented by formula (II)

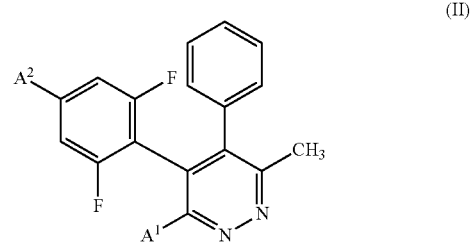

(II)

wherein
$A^1$ represents a chlorine atom, a bromine atom, a cyano group or a methyl group, and
$A^2$ represents a hydrogen atom or a fluorine atom.
[2] The plant disease controlling composition according to [1], wherein a weight ratio of the carboxamide compound and the pyridazine compound satisfies the carboxamide compound/the pyridazine compound=0.1/1 to 10/1.
[3] A method for controlling plant diseases, including a step of applying effective amounts of carboxamide compound represented by formula (I):

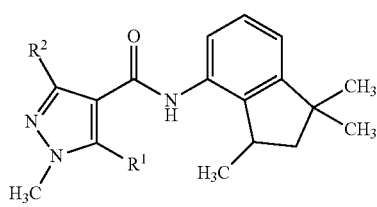

(I)

wherein $R^1$ represents a hydrogen atom or a methyl group and $R^2$ represents a methyl group, a difluoromethyl group or a trifluoromethyl group, and
a pyridazine compound represented by formula (II)

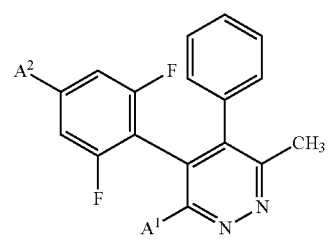

(II)

wherein
$A^1$ represents a chlorine atom, a bromine atom, a cyano group or a methyl group, and
$A^2$ represents a hydrogen atom or a fluorine atom to a plant or soil for growing a plant.
[4] The method for controlling plant diseases according to [3], wherein a weight ratio of the carboxamide compound and the pyridazine compound satisfies the carboxamide compound/the pyridazine compound=0.1/1 to 10/1.

[5] The method for controlling plant diseases according to [3] or [4], wherein the plant or soil for growing a plant is wheat or soil for growing wheat.

Advantageous Effects of Invention

Plant diseases can be controlled by the present invention.

DESCRIPTION OF EMBODIMENTS

The plant disease controlling composition of the present invention (hereinafter, referred to as the composition of the present invention) contains a carboxamide compound represented by formula (I):

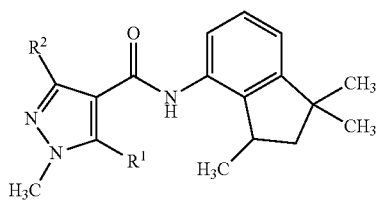

(I)

wherein $R^1$ and $R^2$ are the same as defined above (hereinafter, referred to as the carboxamide compound); and
a pyridazine compound (hereinafter, referred to as the pyridazine compound) represented by formula (II);

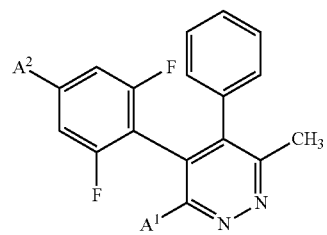

(II)

wherein
$A^1$ represents a chlorine atom, a bromine atom, a cyano group or a methyl group, and
$A^2$ represents a hydrogen atom or a fluorine atom.

The carboxamide compound is a compound described in, for example, International Publication No. WO86/02641 and International Publication No. WO92/12970 and can be produced by the methods described therein.

Specific examples of the carboxamide compound include the following compounds:
a carboxamide compound represented by formula (1) (hereinafter, referred to as the carboxamide compound (1)):

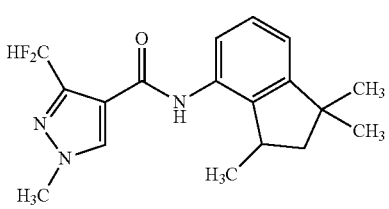

(1)

a carboxamide compound represented by formula (2) (hereinafter, referred to as the carboxamide compound (2)):

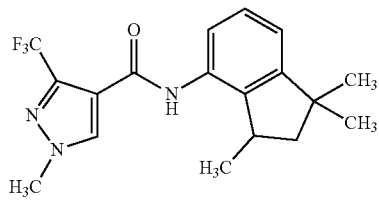

(2)

a carboxamide compound represented by formula (3) (hereinafter, referred to as the carboxamide compound (3)):

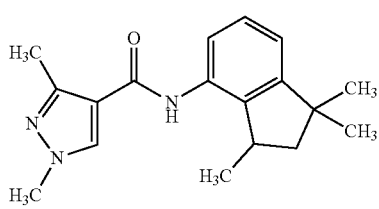

(3)

a carboxamide compound represented by formula (4) (hereinafter, referred to as the carboxamide compound (4)):

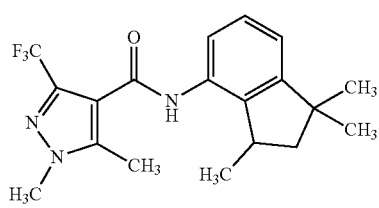

(4)

and
a carboxamide compound represented by formula (5) (hereinafter, referred to as the carboxamide compound (5)):

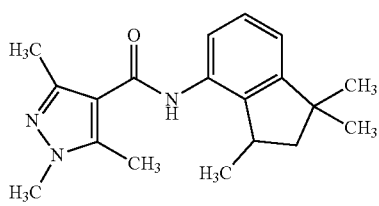

(5)

Examples of the pyridazine compound to be used in the composition of the present invention include the following pyridazine compounds:
A pyridazine compound represented by formula (II) wherein $A^1$ is a chlorine atom or a methyl group;
A pyridazine compound represented by formula (II) wherein $A^1$ is a chlorine atom;
A pyridazine compound represented by formula (II) wherein $A^1$ is a methyl group;
A pyridazine compound represented by formula (II) wherein $A^1$ is a cyano group;

A pyridazine compound represented by formula (II) wherein $A^2$ is a hydrogen atom;

A pyridazine compound represented by formula (II) wherein $A^2$ is a fluorine atom;

A pyridazine compound represented by formula (II) wherein $A^2$ is a chlorine atom or a methyl group and $A^2$ is a hydrogen atom;

A pyridazine compound represented by formula (II) wherein $A^1$ is a chlorine atom or a methyl group and $A^2$ is a fluorine atom.

Specific examples of the pyridazine compound include the following compounds:

a pyridazine compound represented by formula (II) wherein $A^1$ is a chlorine atom and $A^2$ is a hydrogen atom (hereinafter, referred to as the pyridazine compound (1));

a pyridazine compound represented by formula (II) wherein $A^1$ is a bromine atom and $A^2$ is a hydrogen atom (hereinafter, referred to as the pyridazine compound (2));

a pyridazine compound represented by formula (II) wherein $A^1$ is a cyano group and $A^2$ is a hydrogen atom (hereinafter, referred to as the pyridazine compound (3));

a pyridazine compound represented by formula (II) wherein $A^1$ is a methyl group and $A^2$ is a hydrogen atom (hereinafter, referred to as the pyridazine compound (4));

a pyridazine compound represented by formula (II) wherein $A^1$ is a chlorine atom and $A^2$ is a fluorine atom (hereinafter, referred to as the pyridazine compound (5));

a pyridazine compound represented by formula (II) wherein $A^1$ is a bromine atom and $A^2$ is a fluorine atom (hereinafter, referred to as the pyridazine compound (6));

a pyridazine compound represented by formula (II) wherein $A^1$ is a cyano group and $A^2$ is a fluorine atom (hereinafter, referred to as the pyridazine compound (7)); and a pyridazine compound represented by formula (II) wherein $A^1$ is a methyl group and $A^2$ is a fluorine atom (hereinafter, referred to as the pyridazine compound (8)).

Of the pyridazine compounds, the pyridazine compound represented by formula (II) wherein $A^1$ is a chlorine atom or a bromine atom can be produced by a method described, for example, in International Publication No. WO2005/121104.

Of the pyridazine compounds, the pyridazine compound represented by formula (II) wherein $A^1$ is a methyl group can be produced by a method described, for example, in International Publication No. WO2006/001175.

Of the pyridazine compounds, a compound (II-2) represented by formula (II) wherein $A^1$ is a cyano group can be produced by reacting, for example, a compound (II-1) of the pyridazine compounds represented by formula (II) wherein $A^1$ is bromine atom with copper cyanide.

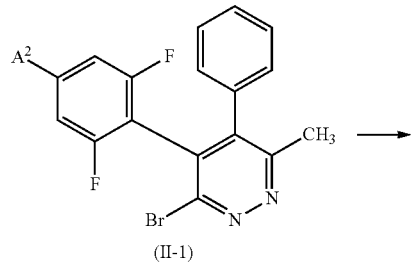

(II-1)

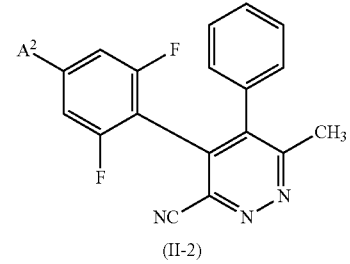

(II-2)

wherein $A^2$ is the same as defined above.

The reaction is usually carried out in the presence of a solvent.

As the solvent to be used in the reaction, for example, an aprotic polar solvent such as N,N-dimethylacetamide is mentioned.

The amount of copper cyanide to be used in the reaction is usually 1 to 1.5 moles relative to 1 mole of compound (II-1) by ratio.

The reaction temperature of the reaction usually falls within the range of 120 to 180° C. and the reaction time usually falls within the range of 1 to 24 hours.

After completion of the reaction, for example, the reaction mixture is mixed with water and an organic solvent and filtrated. After the filtrate is separated, the obtained organic layer is further washed with water, dried and concentrated. Through these operations, the compound (II-2) can be isolated. The isolated compound (II-2) may be further purified by chromatography, recrystallization, and others.

Of the pyridazine compounds, a pyridazine compound (II-4) represented by formula (II) wherein $A^1$ is a methyl group can be produced by reacting a pyridazine compound (II-3) of the pyridazine compounds, represented by formula (II) wherein $A^1$ is a chlorine atom, with a Grignard reagent represented by formula (III):

$$CH_3-MgX \quad (III)$$

wherein X represents a bromine atom or a chlorine atom in the presence of an iron catalyst.

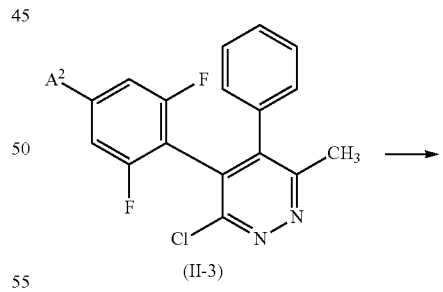

(II-3)

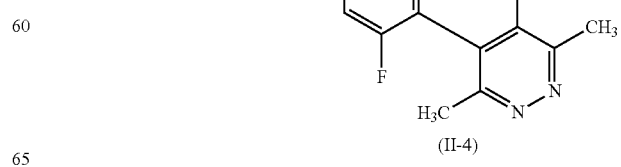

(II-4)

wherein $A^2$ is the same as defined above.

The reaction is carried out usually in the presence of a solvent.

As the solvent to be used in the reaction, for example, tetrahydrofuran, diethylether and N-methylpyrrolidone and a mixture of these are mentioned. In the case where the reaction solvent is a mixture of tetrahydrofuran and N-methylpyrrolidone, the mixing ratio (volume ratio) of tetrahydrofuran to N-methylpyrrolidone usually falls within the range of 30:1 to 3:1.

As the iron catalyst to be used in the reaction, for example, iron (III) acetylacetonate and iron (III) chloride are mentioned. The amount of iron catalyst to be used is usually 0.01 to 0.3 moles relative to 1 mole of the compound (II-3) by ratio.

The reaction temperature of the reaction usually falls within the range of −20° C. to 30° C. and the reaction time usually falls within the range of 0.1 to 6 hours.

After completion of the reaction, for example, the reaction mixture is mixed with hydrochloric acid and extracted with an organic solvent. The obtained organic layer is washed with water, dried and concentrated. Through these operations, the compound (II-4) can be isolated. The isolated compound (II-4) can be further purified by chromatography, recrystallization, and others.

In the composition of the present invention, the weight ratio of the carboxamide compound and the pyridazine compound usually satisfies the carboxamide compound/the pyridazine compound=0.01/1 to 500/1 and preferably 0.1/1 to 10/1.

The composition of the present invention may be a mixture of the carboxamide compound and the pyridazine compound, as it is; however, the composition of the present invention is usually formulated into a preparation by mixing the carboxamide compound, the pyridazine compound and an inactive carrier, optionally adding a surfactant and other preparation adjuvants and preparing an oil solution, an emulsion, a flowable agent, a wettable powder, a granular wettable powder, a powder, a granule, and others. Such a preparation can be used as an agent for controlling plant diseases, directly or as a mixture with other inactive components.

In the composition of the present invention, the carboxamide compound and the pyridazine compound are usually contained in a total amount of 0.1 to 99 wt %, preferably 0.2 to 90 wt % and more preferably 1 to 80 wt %.

Examples of a solid carrier that is used in formulating into a preparation include fine powders or grains formed of minerals such as kaolin clay, Attapulgite clay, bentonite, montmorillonite, acid clay, pyrophyllite, talc, diatom earth and calcite; naturally occurring organic substances such as a corncob powder and a walnut shell flour; synthetic organic substances such as urea; salts such as calcium carbonate and ammonium sulfate; and synthetic inorganic substances such as synthesized water-containing silicon oxide. Examples of a liquid carrier include aromatic hydrocarbons such as xylene, alkylbenzene and methylnaphthalene; alcohols such as 2-propanol, ethylene glycol, propylene glycol and ethylene glycol monoethyl ether; ketones such as acetone, cyclohexanone and isophorone; vegetable oils such as soybean oil and cotton seed oil; petroleum aliphatic hydrocarbons, esters, dimethylsulfoxide, acetonitrile and water.

Examples of a surfactant include anionic surfactants such as an alkyl sulfate, an alkylaryl sulfonate, a dialkylsulfosuccinate, a polyoxyethylene alkylaryl ether phosphate, a lignin sulfonate and a naphthalene sulfonate formaldehyde polycondensate; nonionic surfactants such as polyoxyethylene alkylaryl ether, a polyoxyethylene alkylpolyoxypropylene block copolymer and a sorbitan fatty acid ester; and cationic surfactants such as an alkyltrimethyl ammonium salt.

Examples of other preparation adjuvants include water-soluble polymers such as polyvinyl alcohol and polyvinyl pyrrolidone; polysaccharides such as gum Arabic, alginic acid and a salt thereof, CMC (carboxymethylcellulose) and xanthan gum; inorganic substances such as aluminum magnesium silicate and alumina sol; antiseptic agents, colorants and stabilizers such as PAP (acidic isopropyl phosphate) and BHT.

The composition of the present invention can be also prepared by formulating the carboxamide compound and the pyridazine compound separately into preparations by the aforementioned method, and thereafter, mixing the preparations or, if necessary, diluting them and mixing the dilutions.

The composition of the present invention can be used for protecting plants from plant diseases.

Examples of the plant diseases from which plants are effectively controlled by the composition of the present invention include the following.

Diseases of rice: blast (*Magnaporthe grisea*), *Helminthosporium* leaf spot (*Cochliobolus miyabeanus*), sheath blight (*Rhizoctonia solani*), and bakanae disease (*Gibberella fujikuroi*).

Diseases of wheat: powdery mildew (*Erysiphe graminis*), *Fusarium* head blight (*Fusarium graminearum, F. avenacerum, F. culmorum, Microdochium nivale*), rust (*Puccinia striiformis, P. graminis, P. recondita*), pink snow mold (*Micronectriella nivale*), *Typhula* snow blight (*Typhula* sp.), loose smut (*Ustilago tritici*), bunt (*Tilletia caries*), eyespot (*Pseudocercosporella herpotrichoides*), leaf blotch (*Mycosphaerella graminicola*), glume blotch (*Stagonospora nodorum*), and tan spot (*Pyrenophora tritici-repentis*).

Diseases of barley: powdery mildew (*Erysiphe graminis*), *Fusarium* head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and *Rhizoctonia* damping-off (*Rhizoctonia solani*).

Diseases of corn: smut (*Ustilago maydis*), brown spot (*Cochliobolus heterostrophus*), copper spot (*Gloeocercospora sorghi*), southern rust (*Puccinia polysora*), gray leaf spot (*Cercospora zeae-maydis*), and *Rhizoctonia* damping-off (*Rhizoctonia solani*).

Diseases of citrus: melanose (*Diaporthe citri*), scab (*Elsinoe fawcetti*), *penicillium* rot (*Penicillium digitatum, P. italicum*), and brown rot (*Phytophthora parasitica, Phytophthora citrophthora*).

Diseases of apple: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), and crown rot (*Phytophtora cactorum*).

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophthora cactorum*);

Diseases of peach: brown rot (*Monilinia fructicola*), scab (*Cladosporium carpophilum*), and *phomopsis* rot (*Phomopsis* sp.).

Diseases of grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Diseases of Japanese persimmon: anthracnose (*Gloeosporium kaki*), and leaf spot (*Cercospora kaki, Mycosphaerella nawae*).

Diseases of gourd: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora* sp.), and damping-off (*Pythium* sp.);

Diseases of tomato: early blight (*Alternaria solani*), leaf mold (*Cladosporium fulvum*), and late blight (*Phytophthora infestans*).

Diseases of eggplant: brown spot (*Phomopsis vexans*), and powdery mildew (*Erysiphe cichoracearum*).

Diseases of cruciferous vegetables: *Alternaria* leaf spot (*Alternaria japonica*), white spot (*Cercosporella brassicae*), clubroot (*Plasmodiophora brassicae*), and downy mildew (*Peronospora parasitica*).

Diseases of welsh onion: rust (*Puccinia allii*), and downy mildew (*Peronospora destructor*).

Diseases of soybean: purple seed stain (*Cercospora kikuchii*), sphaceloma scud (*Elsinoe glycines*), pod and stem blight (*Diaporthe phaseolorum* var. *sojae*), septoria brown spot (*Septoria glycines*), frogeye leaf spot (*Cercospora sojina*), rust (*Phakopsora pachyrhizi*), brown stem rot (*Phytophthora sojae*), Rhizoctonia damping-off (*Rhizoctonia solani*) *Corynespora* target spot (*Corynespora casiicola*), and Sclerotinia rot (*Sclerotinia sclerotiorum*).

Diseases of kidney bean: anthracnose (*Colletotrichum lindemthianum*).

Diseases of peanut: leaf spot (*Cercospora personate*), brown leaf spot (*Cercospora arachidicola*) and southern blight (*Sclerotium rolfsii*).

Diseases of garden pea: powdery mildew (*Erysiphe pisi*).

Diseases of potato: early blight (*Alternaria solani*), late blight (*Phytophthora infestans*), pink rot (*Phytophthora erythroseptica*), and powdery scab (*Spongospora subterranean* f. sp. *subterranea*).

Diseases of strawberry: powdery mildew (*Sphaerotheca humuli*), and anthracnose (*Glomerella cingulata*).

Diseases of tea: net blister blight (*Exobasidium reticulatum*), white scab (*Elsinoe leucospila*), gray blight (*Pestalotiopsis* sp.), and anthracnose (*Colletotrichum theae-sinensis*).

Diseases of tobacco: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Diseases of rapeseed: sclerotinia rot (*Sclerotinia sclerotiorum*), and Rhizoctonia damping-off (*Rhizoctonia solani*).

Diseases of cotton: Rhizoctonia damping-off (*Rhizoctonia solani*).

Diseases of sugar beet: Cercospora leaf spot (*Cercospora beticola*), leaf blight (*Thanatephorus cucumeris*), Root rot (*Thanatephorus cucumeris*), and Aphanomyces root rot (*Aphanomyces cochlioides*).

Diseases of rose: black spot (*Diplocarpon rosae*), powdery mildew (*Sphaerotheca pannosa*), and downy mildew (*Peronospora sparsa*).

Diseases of chrysanthemum and asteraceous plants: downy mildew (*Bremia lactucae*), leaf blight (*Septoria chrysanthemi-indici*), and white rust (*Puccinia horiana*).

Diseases of various groups: diseases caused by *Pythium* spp. (*Pythium aphanidermatum, Pythium debarianum, Pythium graminicola, Pythium irregulare, Pythium ultimum*), gray mold (*Botrytis cinerea*), and Sclerotinia rot (*Sclerotinia sclerotiorum*).

Disease of Japanese radish: *Alternaria* leaf spot (*Alternaria brassicicola*).

Diseases of turfgrass: dollar spot (*Sclerotinia homeocarpa*), and brown patch and large patch (*Rhizoctonia solani*).

Disease of banana: sigatoka (*Mycosphaerella fijiensis, Mycosphaerella musicola*).

Disease of sunflower: downy mildew (*Plasmopara halstedii*).

Diseases of seeds or diseases in the initial, stages of crop plants caused by bacteria of e.g., the genus *Aspergillus*, the genus *Penicillium*, the genus *Fusarium*, the genus *Gibberella*, the genus *Tricoderma*, the genus *Thielaviopsis*, the genus *Rhizopus*, the genus *Mucor*, the genus *Corticium*, the genus *Phoma*, the genus *Rhizoctonia* and the genus *Diplodia*.

Viral diseases of crop plants mediated by viruses of e.g., the genus *Polymixa* or the genus *Olpidium*.

Examples of plants to which the composition of the present invention can be applied include the following plants:

crops; corn, rice, wheat, barley, rye, oat, sorghum, cotton, soybean, peanut, buckwheat, beet, rapeseed, sunflower, sugar cane, tobacco, etc.;

vegetables; solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, Dioscorea japonica, colocasia, etc., flowers, foliage plants, turf grasses, fruits; pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, *macadamia* nuts, etc.), berries (blueberry, cranberry, blackberry, raspberry, etc.), grape, kaki fruit, olive, Japanese plum, banana, coffee, date palm, coconuts, etc., trees other than fruit trees; tea, mulberry, flowering plant, roadside trees (ash, birch, dogwood, Eucalyptus, *Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidate*), etc.

The plants mentioned above may include plants which were made resistant by gene recombination techniques.

Of the above diseases, the diseases occurring in wheat, for which a particularly high control efficacy is expected.

Of the plant diseases occurring in these crop plants, examples of diseases of wheat for which a particularly high efficacy is expected include rust (*Puccinia striiformis, P. graminis, P. recondita*), loose smut (*Ustilago tritici*), bunt (*Tilletia caries*), leaf blotch (*Mycosphaerella graminicola*), glume blotch (*Stagonospora nodorum*), and yellow spot (*Pyrenophora tritici-repentis*).

Examples of the composition of the present invention include the following compositions:

a composition containing the carboxamide compound (1) and the pyridazine compound (1);

a composition containing the carboxamide compound (1) and the pyridazine compound (2);

a composition containing the carboxamide compound (1) and the pyridazine compound (3);

a composition containing the carboxamide compound (1) and the pyridazine compound (4);

a composition containing the carboxamide compound (1) and the pyridazine compound (5);

a composition containing the carboxamide compound (1) and the pyridazine compound (6);

a composition containing the carboxamide compound (1) and the pyridazine compound (7);

a composition containing the carboxamide compound (1) and the pyridazine compound (8);

a composition containing the carboxamide compound (2) and the pyridazine compound (1);

a composition containing the carboxamide compound (2) and the pyridazine compound (2);

a composition containing the carboxamide compound (2) and the pyridazine compound (3);

a composition containing the carboxamide compound (2) and the pyridazine compound (4);

a composition containing the carboxamide compound (2) and the pyridazine compound (5);

a composition containing the carboxamide compound (2) and the pyridazine compound (6);

a composition containing the carboxamide compound (2) and the pyridazine compound (7);

a composition containing the carboxamide compound (2) and the pyridazine compound (8);

a composition containing the carboxamide compound (3) and the pyridazine compound (1);

a composition containing the carboxamide compound (3) and the pyridazine compound (2);

a composition containing the carboxamide compound (3) and the pyridazine compound (3);

a composition containing the carboxamide compound (3) and the pyridazine compound (4);

a composition containing the carboxamide compound (3) and the pyridazine compound (5);

a composition containing the carboxamide compound (3) and the pyridazine compound (6);

a composition containing the carboxamide compound (3) and the pyridazine compound (7);

a composition containing the carboxamide compound (3) and the pyridazine compound (8);

a composition containing the carboxamide compound (4) and the pyridazine compound (1);

a composition containing the carboxamide compound (4) and the pyridazine compound (2);

a composition containing the carboxamide compound (4) and the pyridazine compound (3);

a composition containing the carboxamide compound (4) and the pyridazine compound (4);

a composition containing the carboxamide compound (4) and the pyridazine compound (5);

a composition containing the carboxamide compound (4) and the pyridazine compound (6);

a composition containing the carboxamide compound (4) and the pyridazine compound (7);

a composition containing the carboxamide compound (4) and the pyridazine compound (8);

a composition containing the carboxamide compound (5) and the pyridazine compound (1);

a composition containing the carboxamide compound (5) and the pyridazine compound (2);

a composition containing the carboxamide compound (5) and the pyridazine compound (3);

a composition containing the carboxamide compound (5) and the pyridazine compound (4);

a composition containing the carboxamide compound (5) and the pyridazine compound (5);

a composition containing the carboxamide compound (5) and the pyridazine compound (6);

a composition containing the carboxamide compound (5) and the pyridazine compound (7);

a composition containing the carboxamide compound (5) and the pyridazine compound (8);

a composition containing the carboxamide compound (1) and the pyridazine compound (1) in a weight ratio satisfying the carboxamide compound (1)/the pyridazine compound (1)=0.1/1 to 10/1;

a composition containing the carboxamide compound (1) and the pyridazine compound (2) in a weight ratio satisfying the carboxamide compound (1)/the pyridazine compound (2)=0.1/1 to 10/1;

a composition containing the carboxamide compound (1) and the pyridazine compound (3) in a weight ratio satisfying the carboxamide compound (1)/the pyridazine compound (3)=0.1/1 to 10/1;

a composition containing the carboxamide compound (1) and the pyridazine compound (4) in a weight ratio satisfying the carboxamide compound (1)/the pyridazine compound (4)=0.1/1 to 10/1;

a composition containing the carboxamide compound (1) and the pyridazine compound (5) in a weight ratio satisfying the carboxamide compound (1)/the pyridazine compound (5)=0.1/1 to 10/1;

a composition containing the carboxamide compound (1) and the pyridazine compound (6) in a weight ratio satisfying the carboxamide compound (1)/the pyridazine compound (6)=0.1/1 to 10/1;

a composition containing the carboxamide compound (1) and the pyridazine compound (7) in a weight ratio satisfying the carboxamide compound (1)/the pyridazine compound (7)=0.1/1 to 10/1;

a composition containing the carboxamide compound (1) and the pyridazine compound (8) in a weight ratio satisfying the carboxamide compound (1)/the pyridazine compound (8)=0.1/1 to 10/1;

a composition containing the carboxamide compound (2) and the pyridazine compound (1) in a weight ratio satisfying the carboxamide compound (2)/the pyridazine compound (1)=0.1/1 to 10/1;

a composition containing the carboxamide compound (2) and the pyridazine compound (2) in a weight ratio satisfying the carboxamide compound (2)/the pyridazine compound (2)=0.1/1 to 10/1;

a composition containing the carboxamide compound (2) and the pyridazine compound (3) in a weight ratio satisfying the carboxamide compound (2)/the pyridazine compound (3)=0.1/1 to 10/1;

a composition containing the carboxamide compound (2) and the pyridazine compound (4) in a weight ratio satisfying the carboxamide compound (2)/the pyridazine compound (4)=0.1/1 to 10/1;

a composition containing the carboxamide compound (2) and the pyridazine compound (5) in a weight ratio satisfying the carboxamide compound (2)/the pyridazine compound (5)=0.1/1 to 10/1;

a composition containing the carboxamide compound (2) and the pyridazine compound (6) in a weight ratio satisfying the carboxamide compound (2)/the pyridazine compound (6)=0.1/1 to 10/1;

a composition containing the carboxamide compound (2) and the pyridazine compound (7) in a weight ratio satisfying the carboxamide compound (2)/the pyridazine compound (7)=0.1/1 to 10/1;

a composition containing the carboxamide compound (2) and the pyridazine compound (8) in a weight ratio satisfying the carboxamide compound (2)/the pyridazine compound (8)=0.1/1 to 10/1;

a composition containing the carboxamide compound (3) and the pyridazine compound (1) in a weight ratio satisfying the carboxamide compound (3)/the pyridazine compound (1)=0.1/1 to 10/1;

a composition containing the carboxamide compound (3) and the pyridazine compound (2) in a weight ratio satisfying the carboxamide compound (3)/the pyridazine compound (2)=0.1/1 to 10/1;

a composition containing the carboxamide compound (3) and the pyridazine compound (3) in a weight ratio satisfying the carboxamide compound (3)/the pyridazine compound (3)=0.1/1 to 10/1;

a composition containing the carboxamide compound (3) and the pyridazine compound (4) in a weight ratio satisfying the carboxamide compound (3)/the pyridazine compound (4)=0.1/1 to 10/1;

a composition containing the carboxamide compound (3) and the pyridazine compound (5) in a weight ratio satisfying the carboxamide compound (3)/the pyridazine compound (5)=0.1/1 to 10/1;

a composition containing the carboxamide compound (3) and the pyridazine compound (6) in a weight ratio satisfying the carboxamide compound (3)/the pyridazine compound (6)=0.1/1 to 10/1;

a composition containing the carboxamide compound (3) and the pyridazine compound (7) in a weight ratio satisfying the carboxamide compound (3)/the pyridazine compound (7)=0.1/1 to 10/1;

a composition containing the carboxamide compound (3) and the pyridazine compound (8) in a weight ratio satisfying the carboxamide compound (3)/the pyridazine compound (8)=0.1/1 to 10/1;

a composition containing the carboxamide compound (4) and the pyridazine compound (1) in a weight ratio satisfying the carboxamide compound (4)/the pyridazine compound (1)=0.1/1 to 10/1;

a composition containing the carboxamide compound (4) and the pyridazine compound (2) in a weight ratio satisfying the carboxamide compound (4)/the pyridazine compound (2)=0.1/1 to 10/1;

a composition containing the carboxamide compound (4) and the pyridazine compound (3) in a weight ratio satisfying the carboxamide compound (4)/the pyridazine compound (3)=0.1/1 to 10/1;

a composition containing the carboxamide compound (4) and the pyridazine compound (4) in a weight ratio satisfying the carboxamide compound (4)/the pyridazine compound (4)=0.1/1 to 10/1;

a composition containing the carboxamide compound (4) and the pyridazine compound (5) in a weight ratio satisfying the carboxamide compound (4)/the pyridazine compound (5)=0.1/1 to 10/1;

a composition containing the carboxamide compound (4) and the pyridazine compound (6) in a weight ratio satisfying the carboxamide compound (4)/the pyridazine compound (6)=0.1/1 to 10/1;

a composition containing the carboxamide compound (4) and the pyridazine compound (7) in a weight ratio satisfying the carboxamide compound (4)/the pyridazine compound (7)=0.1/1 to 10/1;

a composition containing the carboxamide compound (4) and the pyridazine compound (8) in a weight ratio satisfying the carboxamide compound (4)/the pyridazine compound (8)=0.1/1 to 10/1;

a composition containing the carboxamide compound (5) and the pyridazine compound (1) in a weight ratio satisfying the carboxamide compound (5)/the pyridazine compound (1)=0.1/1 to 10/1;

a composition containing the carboxamide compound (5) and the pyridazine compound (2) in a weight ratio satisfying the carboxamide compound (5)/the pyridazine compound (2)=0.1/1 to 10/1;

a composition containing the carboxamide compound (5) and the pyridazine compound (3) in a weight ratio satisfying the carboxamide compound (5)/the pyridazine compound (3)=0.1/1 to 10/1;

a composition containing the carboxamide compound (5) and the pyridazine compound (4) in a weight ratio satisfying the carboxamide compound (5)/the pyridazine compound (4)=0.1/1 to 10/1;

a composition containing the carboxamide compound (5) and the pyridazine compound (5) in a weight ratio satisfying the carboxamide compound (5)/the pyridazine compound (5)=0.1/1 to 10/1;

a composition containing the carboxamide compound (5) and the pyridazine compound (6) in a weight ratio satisfying the carboxamide compound (5)/the pyridazine compound (6)=0.1/1 to 10/1;

a composition containing the carboxamide compound (5) and the pyridazine compound (7) in a weight ratio satisfying the carboxamide compound (5)/the pyridazine compound (7)=0.1/1 to 10/1;

a composition containing the carboxamide compound (5) and the pyridazine compound (8) in a weight ratio satisfying the carboxamide compound (5)/the pyridazine compound (8)=0.1/1 to 10/1;

The method for controlling plant diseases of the present invention (hereinafter, referred to as the control method of the invention) is carried out by applying effective amounts of the carboxamide compound and the pyridazine compound to a plant or soil for growing a plant. Examples of such a plant include stem and leaves of a plant, seeds of a plant and bulb of a plant. Note that the bulb herein means a bulb, corn, rhizome, stem tuber, root tuber and rhizophore.

In the control method of the invention, the carboxamide compound and the pyridazine compound may be applied simultaneously or separately to a plant or soil for growing a plant; however, they are usually applied in the form of the composition of the present invention, for convenience sake.

In the control method of the invention, as a method for applying the carboxamide compound and the pyridazine compound, for example, application to stem and leaves, application to soil, application to root and application to seeds are mentioned.

As the application to stem and leaves, for example, a method of applying the composition of the present invention to a surface of the plant that is grown, by spraying it to stem and leaves and spraying it to trunk, is mentioned.

As the application to root, for example, a method of soaking a whole plant or root in a drug solution containing the carboxamide compound and the pyridazine compound, and a method of attaching a solid preparation containing the carboxamide compound, the pyridazine compound and a solid carrier, to root of a plant are mentioned.

As the application to soil, for example, spraying, mixing and irrigating of a drug solution to soil are mentioned.

As the application to seeds, for example, application of the composition of the present invention to seeds or bulb of the plant to be protected from plant diseases is mentioned. Specific examples thereof include a mist spray application in which a suspension of the composition of the present invention is converted into mist and sprayed to a seed surface or a bulb surface, a smearing application in which a wettable powder, emulsion or flowable agent of the composition of the present invention is smeared to seeds or bulb by adding a small amount of water to it or directly, soaking application in which seeds are soaked in a solution of the composition of the present invention for a predetermined time, a film-coating application and pellet-coating application.

In the control method of the invention, the application amounts of the carboxamide compound and the pyridazine compound vary depending on e.g., the type of plant to be treated, type and occurrence frequency of plant disease to be controlled, type of a preparation, application time, application method, application site and weather conditions. For example, if the above compounds are applied to plant stem and leaves or soil for growing a plant, the application amounts, i.e., the total amount of the carboxamide compound and the pyridazine compound, are usually 1 to 500 g, preferably 2 to 200 g and more preferably 10 to 100 g per 1000 m$^2$. Furthermore, if applied to seeds, the application amounts of the carboxamide compound and the pyridazine compound, i.e., the total amount of the carboxamide compound and the pyridazine compound, is usually 0.001 to 10 g and preferably 0.01 to 1 g per kg of seeds.

The above emulsion, wettable powder, flowable agent and others are usually diluted with water and then sprayed for treatment. In this case, the concentrations of the carboxamide compound and the pyridazine compound, i.e., the total concentration of the carboxamide compound and the pyridazine compound, is usually 0.0005 to 2 wt % and preferably 0.005 to 1 wt %. The above powder, granules, and the like are usually directly applied without being diluted.

EXAMPLES

The present invention will be further specifically described by way of Preparation Examples and Experimental Examples below; however, the present invention is not limited to the following Examples. Note that, in the following Examples, parts represent parts by weight unless otherwise specified.

First, Reference Production Examples of the pyridazine compound to be used in the composition of the present invention will be further specifically described.

Reference Production Example 1

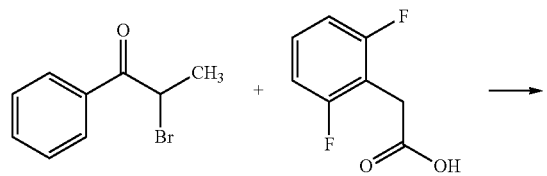

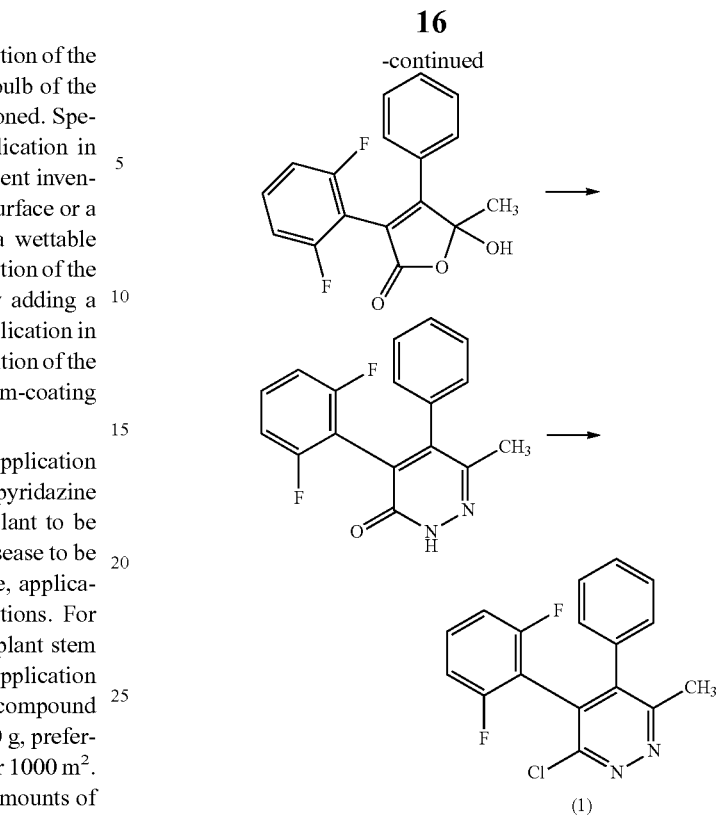

To a mixture of 2-bromopropiophenone (2.13 g), 2,6-difluorophenylacetic acid (1.81 g) and acetonitrile (25 mL, triethylamine (1.52 g) was added dropwise in a water bath, stirred at room temperature for 4 hours and then allowed to stand still overnight. To the mixture, 4.57 g of 1,8-diazabicyclo[5.4.0]-7-undecene (hereinafter, referred to as DBU) was added dropwise under ice cooling. The mixture was stirred at room temperature for one hour. Thereafter, to the obtained mixture, air was blown in while stirring at room temperature for 5 hours. To the reaction mixture, ice and 1 mol/L hydrochloric acid were added. The mixture was extracted with ethyl acetate. The organic layer was sequentially washed with a saturated aqueous sodium bicarbonate solution and a saturated saline solution, dried over an anhydrous magnesium sulfate and concentrated under reduced pressure to obtain 3-(2,6-difluorophenyl)-5-hydroxy-5-methyl-4-phenyl-2 (5H)-furanone (2.83 g).

$^1$H-NMR (CDCl$_3$, TMS) δ (ppm): 1.78 (3H, s), 4.07 (1H, br s), 6.77-6.85 (1H, br m), 6.96-7.08 (1H, m), 7.29-7.38 (4H, m), 7.53-7.55 (2H, m)

To a mixture of 3-(2,6-difluorophenyl)-5-hydroxy-5-methyl-4-phenyl-2(5H)-furanone (2.83 g) and 1-butanol (15 mL), hydrazine monohydrate (0.60 g) was added dropwise and then stirred in a warm bath of 110° C. for 2.5 hours. Subsequently, the reaction mixture was cooled to 0° C. The resultant solid substance was collected by filtration. The collected solid substance was washed with a solvent mixture of hexane and t-butyl methyl ether (1:1) and dried under reduced pressure to obtain 4-(2,6-difluorophenyl)-6-methyl-5-phenyl-2H-pyridazin-3-one (1.70 g).

$^1$H-NMR (DMSO-d6, TMS) δ (ppm): 2.02 (3H, s), 6.92-6.98 (2H, m), 7.11-7.12 (2H, m), 7.27-7.36 (4H, m), 13.2 (1H, br s)

4-(2,6-Difluorophenyl)-6-methyl-5-phenyl-2H-pyridazin-3-one (1.54 g) and phosphorus oxychloride (10 mL)

were mixed and stirred in a warm bath of 110° C. for 1.5 hours. The reaction mixture was allowed to cool to room temperature and then concentrated under reduced pressure. To the residue, ethyl acetate and ice water were added. After the mixture was separated and the organic layer was sequentially washed with a saturated aqueous sodium bicarbonate solution and a saturated saline solution and dried over anhydrous sodium sulfate and then concentrated under reduced pressure. The obtained residue (1.55 g) was washed with a solution mixture of hexane and ethyl acetate (10:1), and subsequently with tert-butyl methyl ether to obtain the pyridazine compound (1) (0.85 g).

$^1$H-NMR (CDCl$_3$, TMS) δ (ppm): 2.55 (3H, s), 6.79-6.83 (2H, m) 7.07-7.09 (2H, m), 7.23-7.30 (4H, m)

Reference Production Example 2

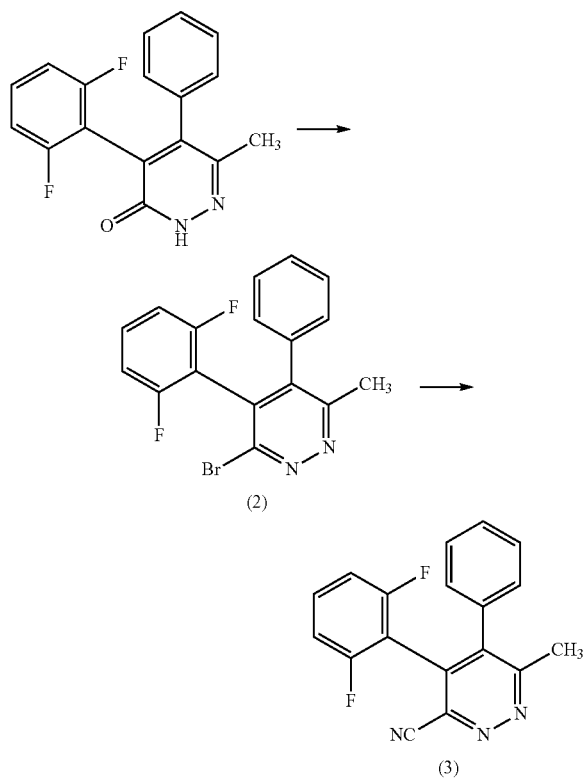

4-(2,6-Difluorophenyl)-6-methyl-5-phenyl-2H-pyridazin-3-one (2.09 g) and phosphorus oxybromide (8.0 g) are mixed and stirred in a warm bath of 85° C. for 1.5 hours and subsequently in a warm bath of 95° C. for one hour. The reaction mixture is allowed to cool to room temperature, suspended in ethyl acetate (about 20 mL) and poured in ice (about 100 g). After the obtained solution is neutralized with sodium bicarbonate water, the residue is extracted with ethyl acetate and separated. The organic layer is washed with a saline solution, dried over anhydrous magnesium sulfate and concentrated under reduced pressure. The obtained residue is subjected to silica gel column chromatography to obtain the pyridazine compound (2).

The pyridazine compound (2) (0.72 g), copper cyanide (0.22 g) and N,N-dimethylacetamide (6 mL) are mixed and stirred under heat reflux for 3 hours. The reaction mixture is allowed to cool to room temperature, added to ethyl acetate and water (about 50 mL for each) and filtrated with cerite. The filtrate is separated and the organic layer is washed with a saline solution, dried over anhydrous magnesium sulfate and concentrated under reduced pressure. The obtained residue is subjected to silica gel column chromatography to obtain the pyridazine compound (3).

Reference Production Example 3

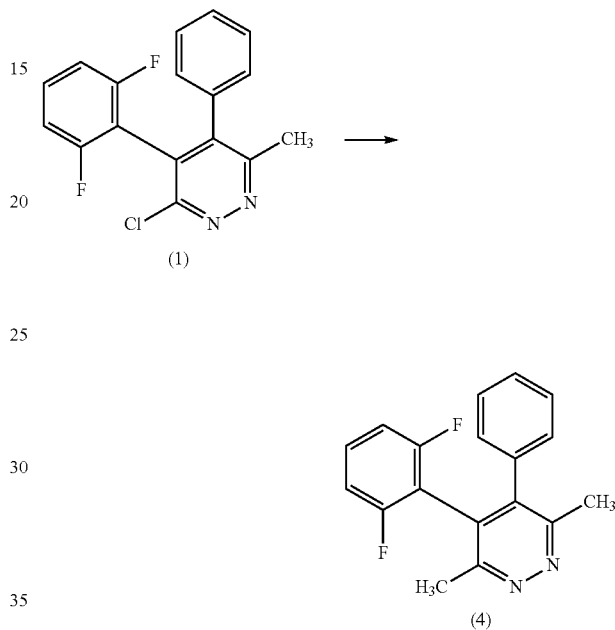

The pyridazine compound (1) (1.90 g), iron (III) acetylacetonate (0.42 g), tetrahydrofuran (60 mL) and N-methylpyrrolidone (6 mL) are mixed. To this, methylmagnesium bromide (3.0 mol/L diethylether solution) (6 mL) is added while stirring under ice cooling. To the reaction mixture, a 1 mol/L aqueous hydrochloric acid solution (30 mL) is added dropwise and water is added. Thereafter, the reaction mixture is extracted with ethyl acetate. The organic layer is sequentially washed with sodium bicarbonate water and a saline solution, dried over anhydrous magnesium sulfate and concentrated under reduced pressure. The obtained residue is subjected to silica gel column chromatography to obtain the pyridazine compound (4).

Reference Production Example 4

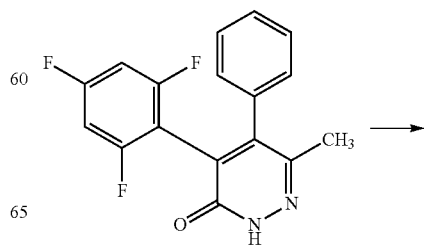

-continued

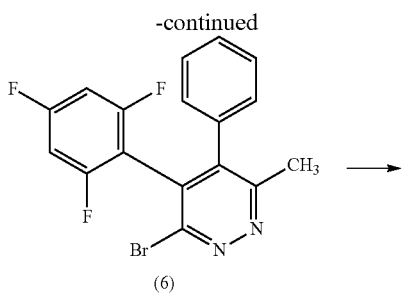

(6)

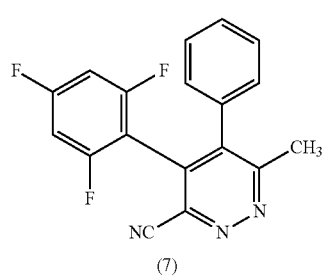

(7)

6-Methyl-5-phenyl-4-(2,4,6-trifluorophenyl)-2H-pyridazin-3-one (2.21 g) and phosphorus oxybromide (8.0 g) are mixed and stirred in a warm bath of 85° C. for 1.5 hours and subsequently in a warm bath of 95° C. for one hour. The reaction mixture is allowed to cool to room temperature, suspended in ethyl acetate (about 20 mL) and poured in ice (about 100 g). After the obtained solution is neutralized with sodium bicarbonate water, the residue is extracted with ethyl acetate and separated. The organic layer is washed with a saline solution, dried over anhydrous magnesium sulfate and concentrated under reduced pressure. The obtained residue is subjected to silica gel column chromatography to obtain the pyridazine compound (6).

The pyridazine compound (6) (0.76 g), copper cyanide (0.22 g) and N,N-dimethylacetamide (6 mL) are mixed and stirred under heat reflux for 3 hours. The reaction mixture is allowed to cool to room temperature, added to ethyl acetate and water (about 50 mL for each) and filtrated with cerite. The filtrate is separated and the organic layer is washed with a saline solution, dried over anhydrous magnesium sulfate and concentrated under reduced pressure. The obtained residue is subjected to silica gel column chromatography to obtain the pyridazine compound (7).

Reference Production Example 5

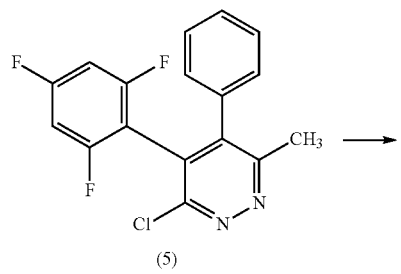

(5)

-continued

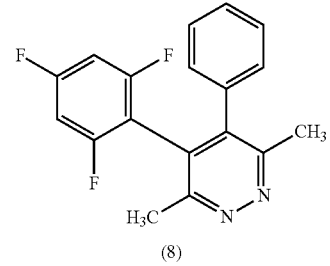

(8)

The pyridazine compound (5) (2.01 g), iron (III) acetylacetonate (0.42 g), tetrahydrofuran (60 mL) and N-methylpyrrolidone (6 mL) are mixed. To this, methylmagnesium bromide (3.0 mol/L diethylether solution) (6 mL) is added while stirring under ice cooling. To the reaction mixture, a 1 mol/L aqueous hydrochloric acid solution (30 mL) is added dropwise and water is added. The reaction mixture is then extracted with ethyl acetate. The organic layer is sequentially washed with sodium bicarbonate water and a saline solution, dried over anhydrous magnesium sulfate and concentrated under reduced pressure. The obtained residue is subjected to silica gel column chromatography to obtain the pyridazine compound (8).

Next, Preparation Examples will be described.

Preparation Example 1

The carboxamide compound (1) (2.5 parts), each of the pyridazine compounds (1) to (8) (1.25 parts), polyoxyethylene styryl phenyl ether (14 parts), calcium dodecylbenzene sulfonate (6 parts) and xylene (76.25 parts) are mixed well. In this manner, preparations are obtained.

Preparation Example 2

The carboxamide compound (2) (2.5 parts), each of the pyridazine compounds (1) to (8) (1.25 parts), polyoxyethylene styryl phenyl ether (14 parts), calcium dodecylbenzene sulfonate (6 parts) and xylene (76.25 parts) are mixed well. In this manner, preparations are obtained.

Preparation Example 3

The carboxamide compound (3) (2.5 parts), each of the pyridazine compounds (1) to (8) (1.25 parts), polyoxyethylene styryl phenyl ether (14 parts), calcium dodecylbenzene sulfonate (6 parts) and xylene (76.25 parts) are mixed well. In this manner, preparations are obtained.

Preparation Example 4

The carboxamide compound (4) (2.5 parts), each of the pyridazine compounds (1) to (8) (1.25 parts), polyoxyethylene styryl phenyl ether (14 parts), calcium dodecylbenzene sulfonate (6 parts) and xylene (76.25 parts) are mixed well. In this manner, preparations are obtained.

Preparation Example 5

The carboxamide compound (5) (2.5 parts), each of the pyridazine compounds (1) to (8) (1.25 parts), polyoxyethylene styryl phenyl ether (14 parts), calcium dodecylbenzene sulfonate (6 parts) and xylene (76.25 parts) are mixed well. In this manner, preparations are obtained.

Preparation Example 6

The carboxamide compound (1) (2 parts), each of the pyridazine compounds (1) to (8) (8 parts), a mixture of white carbon and polyoxyethylene alkyl ether sulfate ammonium salt (in a weight ratio of 1:1) (35 parts) and water (55 parts) are mixed and fine-ground by a wet grinding method. In this manner, preparations are obtained.

Preparation Example 7

The carboxamide compound (2) (2 parts), each of the pyridazine compounds (1) to (8) (8 parts), a mixture of white carbon and polyoxyethylene alkyl ether sulfate ammonium salt in a weight ratio of 1:1) (35 parts) and water (55 parts) are mixed and fine-ground by a wet grinding method. In this manner, preparations are obtained.

Preparation Example 8

The carboxamide compound (3) (2 parts), each of the pyridazine compounds (1) to (8) (8 parts), a mixture of white carbon and polyoxyethylene alkyl ether sulfate ammonium salt (in a weight ratio of 1:1) (35 parts) and water (55 parts) are mixed and fine-ground by a wet grinding method. In this manner, preparations are obtained.

Preparation Example 9

The carboxamide compound (4) (2 parts), each of the pyridazine compounds (1) to (8) (8 parts), a mixture of white carbon and polyoxyethylene alkyl ether sulfate ammonium salt in a weight ratio of 1:1) (35 parts) and water (55 parts) are mixed and fine-ground by a wet grinding method. In this manner, preparations are obtained.

Preparation Example 10

The carboxamide compound (5) (2 parts), each of the pyridazine compounds (1) to (8) (8 parts), a mixture of white carbon and polyoxyethylene alkyl ether sulfate ammonium salt (in a weight ratio of 1:1) (35 parts) and water (55 parts) are mixed and fine-ground by a wet grinding method. In this manner, preparations are obtained.

Preparation Example 11

The carboxamide compound (1) (5 parts), each of the pyridazine compounds (1) to (8) (10 parts), sorbitan trioleate (1.5 parts) and an aqueous solution (28.5 parts) containing polyvinyl alcohol (2 parts) are mixed and fine-ground by a wet grinding method. To the obtained ground product, an aqueous solution (45 parts) containing xanthan gum (0.05 parts) and aluminum magnesium silicate (0.1 parts) is added, and further propylene glycol (10 parts) is added and stirred. In this manner, preparations are obtained.

Preparation Example 12

The carboxamide compound (2) (5 parts), each of the pyridazine compounds (1) to (8) (10 parts), sorbitan trioleate (1.5 parts) and an aqueous solution (28.5 parts) containing polyvinyl alcohol (2 parts) are mixed and fine-ground by a wet grinding method. To the obtained ground product, an aqueous solution (45 parts) containing xanthan gum (0.05 parts) and aluminum magnesium silicate (0.1 parts) is added, and further propylene glycol (10 parts) is added and stirred. In this manner, preparations are obtained.

Preparation Example 13

The carboxamide compound (3) (5 parts), each of the pyridazine compounds (1) to (8) (10 parts), sorbitan trioleate (1.5 parts) and an aqueous solution (28.5 parts) containing polyvinyl alcohol (2 parts) are mixed and fine-ground by a wet grinding method. To the obtained ground product, an aqueous solution (45 parts) containing xanthan gum (0.05 parts) and aluminum magnesium silicate (0.1 parts) is added, and further propylene glycol (10 parts) is added and stirred. In this manner, preparations are obtained.

Preparation Example 14

The carboxamide compound (4) (5 parts), each of the pyridazine compounds (1) to (8) (10 parts), sorbitan trioleate (1.5 parts) and an aqueous solution (28.5 parts) containing polyvinyl alcohol (2 parts) are mixed and fine-ground by a wet grinding method. To the obtained ground product, an aqueous solution (45 parts) containing xanthan gum (0.05 parts) and aluminum magnesium silicate (0.1 parts) is added, and further propylene glycol (10 parts) is added and stirred. In this manner, preparations are obtained.

Preparation Example 15

The carboxamide compound (5) (5 parts), each of the pyridazine compounds (1) to (8) (10 parts), sorbitan trioleate (1.5 parts) and an aqueous solution (28.5 parts) containing polyvinyl alcohol (2 parts) are mixed and fine-ground by a wet grinding method. To the obtained ground product, an aqueous solution (45 parts) containing xanthan gum (0.05 parts) and aluminum magnesium silicate (0.1 parts) is added, and further propylene glycol (10 parts) is added and stirred. In this manner, preparations are obtained.

Preparation Example 16

The carboxamide compound (1) (1 part), each of the pyridazine compounds (1) to (8) (4 parts), synthesized water-containing silicon oxide (1 part), calcium ligninsulfonate (2 parts), bentonite (30 parts) and kaolin clay (62 parts) are ground and mixed well. To this, water is added. The mixture is sufficiently kneaded, granulated and dried. In this manner, preparations are obtained.

Preparation Example 17

The carboxamide compound (2) (1 part), each of the pyridazine compounds (1) to (8) (4 parts), synthesized water-containing silicon oxide (1 part), calcium ligninsulfonate (2 parts), bentonite (30 parts) and kaolin clay (62 parts) are ground and mixed well. To this, water is added. The mixture is sufficiently kneaded, granulated and dried. In this manner, preparations are obtained.

Preparation Example 18

The carboxamide compound (3) (1 part), each of the pyridazine compounds (1) to (8) (4 parts), synthesized water-containing silicon oxide (1 part), calcium ligninsulfonate (2 parts), bentonite (30 parts) and kaolin clay (62 parts) are ground and mixed well. To this, water is added. The mixture is sufficiently kneaded, granulated and dried. In this manner, preparations are obtained.

Preparation Example 19

The carboxamide compound (4) (1 part), each of the pyridazine compounds (1) to (8) (4 parts), synthesized water-containing silicon oxide (1 part), calcium ligninsulfonate (2 parts), bentonite (30 parts) and kaolin clay (62 parts) are ground and mixed well. To this, water is added. The mixture is sufficiently kneaded, granulated and dried. In this manner, preparations are obtained.

Preparation Example 20

The carboxamide compound (5) (1 part), each of the pyridazine compounds (1) to (8) (4 parts), synthesized water-containing silicon oxide (1 part), calcium ligninsulfonate (2 parts), bentonite (30 parts) and kaolin clay (62 parts) are ground and mixed well. To this, water is added. The mixture is sufficiently kneaded, granulated and dried. In this manner, preparations are obtained.

Preparation Example 21

The carboxamide compound (1) (12.5 parts), each of the pyridazine compounds (1) to (8) (37.5 parts), calcium lignin-sulfonate (3 parts), sodium lauryl sulfate (2 parts) and synthesized water-containing silicon oxide (45 parts) are ground and mixed well. In this manner, preparations are obtained.

Preparation Example 22

The carboxamide compound (1) (12.5 parts), each of the pyridazine compounds (1) to (8) (37.5 parts), calcium lignin-sulfonate (3 parts), sodium lauryl sulfate (2 parts) and synthesized water-containing silicon oxide (45 parts) are ground and mixed well. In this manner, preparations are obtained.

Preparation Example 23

The carboxamide compound (3) (12.5 parts), each of the pyridazine compounds (1) to (8) (37.5 parts), calcium lignin-sulfonate (3 parts), sodium lauryl sulfate (2 parts) and synthesized water-containing silicon oxide (45 parts) are ground and mixed well. In this manner, preparations are obtained.

Preparation Example 24

The carboxamide compound (4) (12.5 parts), each of the pyridazine compounds (1) to (8) (37.5 parts), calcium lignin-sulfonate (3 parts), sodium lauryl sulfate (2 parts) and synthesized water-containing silicon oxide (45 parts) are ground and mixed well. In this manner, preparations are obtained.

Preparation Example 25

The carboxamide compound (5) (12.5 parts), each of the pyridazine compounds (1) to (8) (37.5 parts), calcium lignin-sulfonate (3 parts), sodium lauryl sulfate (2 parts) and synthesized water-containing silicon oxide (45 parts) are ground and mixed well. In this manner, preparations are obtained.

Preparation Example 26

The carboxamide compound (1) (3 parts), each of the pyridazine compounds (1) to (8) (2 parts), kaolin clay (85 parts) and talc (1.0 parts) are ground and mixed well. In this manner, preparations are obtained.

Preparation Example 27

The carboxamide compound (2) (3 parts), each of the pyridazine compounds (1) to (8) (2 parts), kaolin clay (85 parts) and talc (10 parts) are ground and mixed well. In this manner, preparations are obtained.

Preparation Example 28

The carboxamide compound (3) (3 parts), each of the pyridazine compounds (1) to (8) (2 parts), kaolin clay (85 parts) and talc (10 parts) are ground and mixed well. In this manner, preparations are obtained.

Preparation Example 29

The carboxamide compound (4) (3 parts), each of the pyridazine compounds (1) to (8) (2 parts), kaolin clay (85 parts) and talc (10 parts) are ground and mixed well. In this manner, preparations are obtained.

Preparation Example 30

The carboxamide compound (5) (3 parts), each of the pyridazine compounds (1) to (8) (2 parts), kaolin clay (85 parts) and talc (10 parts) are ground and mixed well. In this manner, preparations are obtained.

Next, Experimental Examples will be described.

Experimental Example 1

A plastic pot was charged with soil. To the soil, wheat seeds (cultivar; Apogee) were seeded and grown for 14 days in a greenhouse. A test compound was dissolved in CEC cocktail (cyclohexanone: Sorpol (registered trade mark) 2680X (manufactured by TOHO Chemical Industry Co., Ltd.)=5:1 (volume ratio)) to make a preparation. Thereafter, the preparation was diluted with water up to a predetermined concentration. The diluted solution was sprayed to stem and leaves such that the diluted solution was sufficiently attached to the leaf surfaces of the wheat. After spraying, the plant was air-dried. Two days later, an aqueous suspension (about 1,000,000/mL) containing conidiospores of wheat leaf blotch (*Mycosphaerella graminicola*) was sprayed to inoculate the spores. After completion of the inoculation, the plant was allowed to leave first in a high-humidity place at 18° C. for 3 days and then the plant was taken out from the high-humidity place and transferred to a thermostatic chamber of 18° C. for 14 days. In this manner, wheat was grown (this is referred to as a treatment district). Thereafter, the lesion area of wheat leaf blotch was checked.

On the other hand, wheat was grown in the same manner as in the treatment district except that a diluted solution of a test compound was not sprayed to stein and leaves (this is referred to as a non-treatment district). The lesion area of wheat leaf blotch was checked in the same manner as in the treatment district.

From the lesion areas of the treatment district and the non-treatment district, the efficacy of the treatment district was obtained in accordance with the following expression (1). The results are shown in [Table 1] to [Table 4].

$$\text{Efficacy (\%)} = \left(1 - \frac{\text{Lesion area of treatment district}}{\text{Lesion area of non-treatment district}}\right) \times 100 \quad \text{Expression (1)}$$

TABLE 1

| The carboxamide compound (1) [ppm] | The pyridazine compound (1) [ppm] | Efficacy (%) |
|---|---|---|
| 3.1 | 3.1 | 100 |

TABLE 2

| The carboxamide compound (4) [ppm] | The pyridazine compound (5) [ppm] | Efficacy (%) |
|---|---|---|
| 3.1 | 3.1 | 100 |

TABLE 3

| The carboxamide compound (1) [ppm] | The pyridazine compound (1) [ppm] | Efficacy (%) |
|---|---|---|
| 3.1 | 3.1 | 100 |

TABLE 4

| The carboxamide compound (4) [ppm] | The pyridazine compound (5) [ppm] | Efficacy (%) |
|---|---|---|
| 3.1 | 3.1 | 100 |

Experimental Example 2

By use of a rotatory seed processor (seed dresser, manufactured by Hans-Ulrich liege GmbH), a cyclohexanone solution (100 μL) on containing a predetermined weight of a test compound was smeared to wheat (cultivar; Shirogane) seeds (10 g) naturally infected with spores of pink snow mold (*Microdochium nivale*).

One day after the treatment, a plastic pot was charged with soil and the seeds treated with the test compound were seeded to the soil and grown in a greenhouse made of glass for 20 days (this is referred to as a treatment district). Thereafter, seedlings obtained from individual seeds by budding were observed for onset of pink snow mold and an incidence rate of the disease was obtained in accordance with the following expression (2).

On the other hand, wheat seeds not treated with the smearing treatment mentioned above were grown in the same manner as in the treatment district (this is referred to as a non-treatment district). An incidence rate of the disease was obtained in the same manner as in the treatment district.

As a result, the incidence rate of the seedlings obtained from wheat seeds by budding and treated with the composition of the present invention was lower than that of the seedlings of the non-treatment district.

From the lesion areas of the treatment district and the non-treatment district, the efficacy in the treatment district was obtained in accordance with the following expression (1). The results are shown in [Table 5] to [Table 6].

$$\text{Incidence rate (\%)} = \left(1 - \frac{\text{Number of onset seedlings}}{\text{Number of total seedlings}}\right) \times 100 \quad \text{Expression (2)}$$

$$\text{Efficacy (\%)} = \left(1 - \frac{\text{Incidence rate of the treatment district}}{\text{Incidence rate of the non-treatment district}}\right) \times 100 \quad \text{Expression (3)}$$

TABLE 5

| The carboxamide compound (1) [g/100 kg Seeds] | The pyridazine compound (1) [g/100 kg Seeds] | Efficacy (%) |
|---|---|---|
| 5 | 5 | 100 |

TABLE 6

| The carboxamide compound (1) [g/100 kg Seeds] | The pyridazine compound (5) [g/100 kg Seeds] | Efficacy (%) |
|---|---|---|
| 5 | 5 | 100 |

The invention claimed is:

1. A plant disease controlling composition, comprising a carboxamide compound represented by formula (I):

(I)

wherein $R^1$ represents a hydrogen atom or a methyl group and $R^2$ represents a methyl group, a difluoromethyl group or a trifluoromethyl group, and a pyridazine compound represented by formula (II):

(II)

wherein $A^1$ represents a chlorine atom, a bromine atom, a cyano group or a methyl group, and $A^2$ represents a hydrogen atom or a fluorine atom.

2. The plant disease controlling composition according to claim 1, wherein a weight ratio of the carboxamide compound to the pyridazine compound is in a range of 0.1/1 to 10/1.

3. A method for controlling plant diseases, comprising a step of applying to a plant or soil for growing a plant effective amounts of a carboxamide compound represented by formula (I):

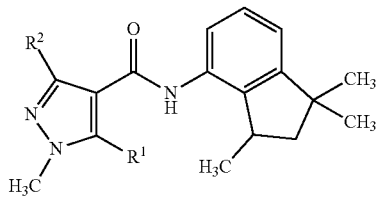

(I)

wherein $R^1$ represents a hydrogen atom or a methyl group and $R^2$ represents a methyl group, a difluoromethyl group or a trifluoromethyl group, and a pyridazine compound represented by formula (II):

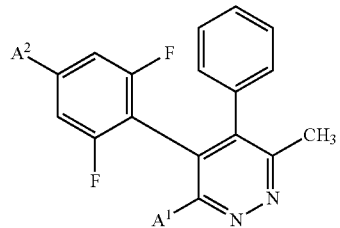

(II)

wherein $A^1$ represents a chlorine atom, a bromine atom, a cyano group or a methyl group, and $A^2$ represents a hydrogen atom or a fluorine.

4. The method for controlling plant diseases according to claim 3, wherein a weight ratio of the carboxamide compound to the pyridazine compound is in a range of 0.1/1 to 10/1.

5. The method for controlling plant diseases according to claim 3, wherein the plant or soil for growing a plant is wheat or soil for growing wheat.

6. The method for controlling plant diseases according to claim 4, wherein the plant or soil for growing a plant is wheat or soil for growing wheat.

\* \* \* \* \*